US00PP20428P3

(12) United States Plant Patent

Skirvin et al.

(10) Patent No.: US PP20,428 P3

(45) Date of Patent: Oct. 20, 2009

(54) GRAPE PLANT NAMED 'IMPROVED CHANCELLOR'

(50) Latin Name: *Vitis vinifera*
Varietal Denomination: Improved Chancellor

(75) Inventors: Robert M. Skirvin, Champaign, IL (US); Margaret A. Norton, Urbana, IL (US); Stephen K. Farrand, Seymour, IL (US); Richard M. S. Mulwa, Msambweni (KE)

(73) Assignee: The Board of Trustees of the Unviersity of Illinois, Urbana, IL (US)

( * ) Notice: Subject to any disclaimer, the term of this patent is extended or adjusted under 35 U.S.C. 154(b) by 248 days.

(21) Appl. No.: 11/206,645

(22) Filed: Aug. 17, 2005

(65) Prior Publication Data

US 2007/0044185 P1 Feb. 22, 2007

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

| | | | |
|---|---|---|---|
| 6,153,401 | A | 11/2000 | Streber et al. |
| 6,455,312 | B1 | 9/2002 | Gray et al. |
| 2003/0154507 | A1 | 8/2003 | Oliver et al. |

OTHER PUBLICATIONS

Bayley et al., (1992) "Engineering 2, 4–D Resistance into Cotton," *Theoretical Appl. Genetics* 83:645–649.

Chien, M. (2001) "2, 4–D Herbicide Drift into Vineyards," *The Grapevine Newsletter, Jan. 2001, Penn. State Cooperative Extension Agency*.

Hébert et al. (1993) "Optimization of Biolistic Transformation of Embryogenic Grape Cell Suspensions," *Plant Cell Reports* 12:585–589.

Hébert–Soulé et al. (1995) "Phosphinothricin Stimulates Somatic Embryogenesis in Grape (*Vitis* sp. L.)," *Plant Cell Reports* 14:380–384.

Hellman et al., (1999) Preventing Phenoxy Herbicide Damage to Grape Vineyards, Oregon State University Extension Service, Printed from eesc.orst.edu/agcomwebfile/admat/html on the internet.

Hellman, E.W. (1987) "Cultivar Sensivity of Grapevines to 2, 4–D," *Fruit Varieties J.* 41:111–114.

Iocco et al., (2001) "Genetic Transformation of Major Wine Grape Cultivars of *Vitis vinifera* L.," *Transgenic Res.,* 10:105–112.

Last et al., (1999) "A Detoxification Gene in Transgenic *Nicotiana tabacum* Confers 2, 4–D Tolerance," *Weed Sci.* 47:401–404.

Levenko et al., (2000) "Herbicide Resistant Transgenic Plants of Grapevine," *Acta Horticulturae* 528:337–339.

Motoike et al., (2002) "Development of Methods of Genetically Transform American Grape (*Vitis×labruscana* L. H. Baily)," *J. Hortic. Sci. Biotechnol.* 77:691–696.

Norton et al., (2001) "Micropropagation of 'Norton' Wine grape," *Hortechnology* 11:18–20.

Oxtoby et al. (1990) "Engineering Herbicide Tolerance into Crops," *Trends in Biotechnol.* 8:61–65.

Perl et al. (1996) "Regeneration and Transformation of Grape (*Vitis vinifera* L.)," *Plant Tissue Culture Biotechnol.* 2:187–193.

Robinson et al. (1978) "2, 4–D Herbicides in Central Washington," *J. Air Pollution Control Association* 28:1015–1020.

Skirvin et al. (2005) "Grape Varieties for the Different Regions of Illinois," *Proc 2005 Illinois Small Fruit and Strawberry Schools, NRES* 7:29–40.

Streber et al. (1987) "Analysis, Cloning, and High Level Expression of 2, 4–Dichlorophenoxyacetate Monooxygenase Gene *tfdA* of *Alcaligenes eutrophus* JMP134," *J. Bacteriol.* 169:2950–2955.

Streber et al., (1989) "Transgenic Tobacco Plants Expressing a Bacterial Detoxifying Enzyme are Resistant to 2, 4–D," *Bio/Technology* 7:811–816.

Thomas et al., (2000) "Transgenic Grapevines: Status and Future," *Acta Horticulturae* 528:279–287.

*Primary Examiner*—Kent L Bell

(74) *Attorney, Agent, or Firm*—Greenlee, Winner and Sullivan, P.C.

(57) ABSTRACT

A new and distinct transgenic grape plant *Vitis vinifera* called "Improved Chancellor" which is characterized by greater tolerance to 2,4-diphenoxyacetic acid than is the parent Chancellor grape plant.

2 Drawing Sheets

Genus: *Vitis* (complex interspecific hybrid lineage).

BACKGROUND AND SUMMARY OF THE INVENTION

The new grape plant named 'Improved Chancellor' is of *Vitis* parentage, with the breeding chart tracing the lineage as shown in FIG. 3.

The new grapevine resulted from stably introducing a plant expressible tfdA gene from *Ralstonia eutrophus* into Chancellor grapes. The tdfA gene confers resistance in plants to the phenoxy herbicides, especially 2,4 D (2,4-diphenoxyacetic acid). For a general discussion, see U.S. Pat. Publication No. 2003-0154507. This resistance improves the performance of grapevines, which are by nature exquisitely sensitive to the phenoxy herbicides, with deleterious effects observed with drift of herbicide from fields in the area, especially grain fields sprayed to control broadleaf weeds. Damage from drift negatively affects growth and/or yield in affected vineyards.

DESCRIPTION OF THE INVENTION

The transgenic 2, 4-D resistant 'Chancellor' grape was produced via genetic engineering. Embryogenic callus was initiated from ovary explants dissected from flower buds 10–14 days before anthesis on Nistch and Nistch (1969) medium containing 9 μM 2, 4-D, 17 μM IASP, and 1 μM BAP in darkness. Embryogenic callus was proliferated and maintained in NN medium containing 2 μM 2, 4-D, 0.2 μM TDZ and 4 μM IASP (Long Term Maintenance Medium, LTMM). Embryogenic callus cultivated for 5 weeks in LTMM was infected with *Agrobacterium tumefaciens* strain LBA4404:pAL4404 carrying a pBIN19 plant transformation plasmid vector containing the tfdA gene construct. The 864 bp tfdA gene in the construct is driven by the CaMV35S core promoter and linked to the nos gene terminator. Transformed embryogenic cells were selected on LTMM containing 350 mg $l^{-1}$ kanamycin and induced to develop somatic embryos on NN medium supplemented with 10 μM IASP, 8 μM NOA, 1 μM TDZ, 1 μM ABA and 2.5 g $l^{-1}$ activated charcoal (Embryo Development and Maturation Medium, EDMM). Somatic embryos were germinated and converted into plantlets in ½ MS (Murashige & Skoog, 1962) medium containing 0.5 μM BA+0.025 μM NAA. PCR analysis of regenerated plantlets with tfdA-specific primers showed they contained the tfdA gene. The expression of the tfdA gene in the transgenic plants was demonstrated by their 2, 4-D resistance during spray tests. Transgenic plants survived treatment with 0.5, 5, and 10 kg $ha^{-1}$ of 2-ethylhexyl ester of 2, 4-D. These rates killed non-transgenic plants.

Spray tests utilized applications of 2,4D corresponding to field application rates of 0, 0.5, 5 and 10 kg/ha of a commercial herbicide preparation (LV400, Growmark Inc). After spraying, the transgenic plant and wild type plants were allowed to dry and then transferred to an isolation greenhouse, and they were observed for damage over a period of three weeks. The wild type plants showed signs of damage within two hours of spraying and they were all dead within one week. While the transgenic plant showed minor, short lived injury (leaf epinasty) for up to seven days at the 2 higher doses of 2 4-D, there was full recovery, with normal growth at the end of two weeks.

The original vine of 'Improved Chancellor' arose from selection among embryogenic cells developed in vitro. The cells had been transformed with the tfdA gene. About 20 plants were regenerated between 2002 and 2003; 'Improved Chancellor' was selected from these. It was then micropropagated by cuttings in Urbana, Ill. Those resulting plants were stable and typical of the original vine. 'Improved Chancellor's' resistance to 2,4-D was confirmed in 2004 in the original plant and in asexually propagated material from the original plant. Subsequent asexual propagations of the variety have also proven stable with true to type plants.

COMPARISON WITH PARENTAL CULTIVAR

The new grape plant named 'Improved Chancellor' resembles the parent grape, from which it was produced by genetic modification, but it differs in that it is significantly less sensitive to herbicide 2,4-D. The fruit color, flavor and texture is expected to be similar to the original grape. Vigor of the new variety is the same as the parent plant in absence of herbicide. However, vigor of 'Improved Chancellor' is increased over that of the parent plant in the presence of herbicide.

DESCRIPTION OF THE FIGURES

FIG. 3 Shows the breeding chart tracing the lineage of 'Improved Chancellor'.

DETAILED BOTANICAL DESCRIPTION OF THE INVENTION

Figure 1:
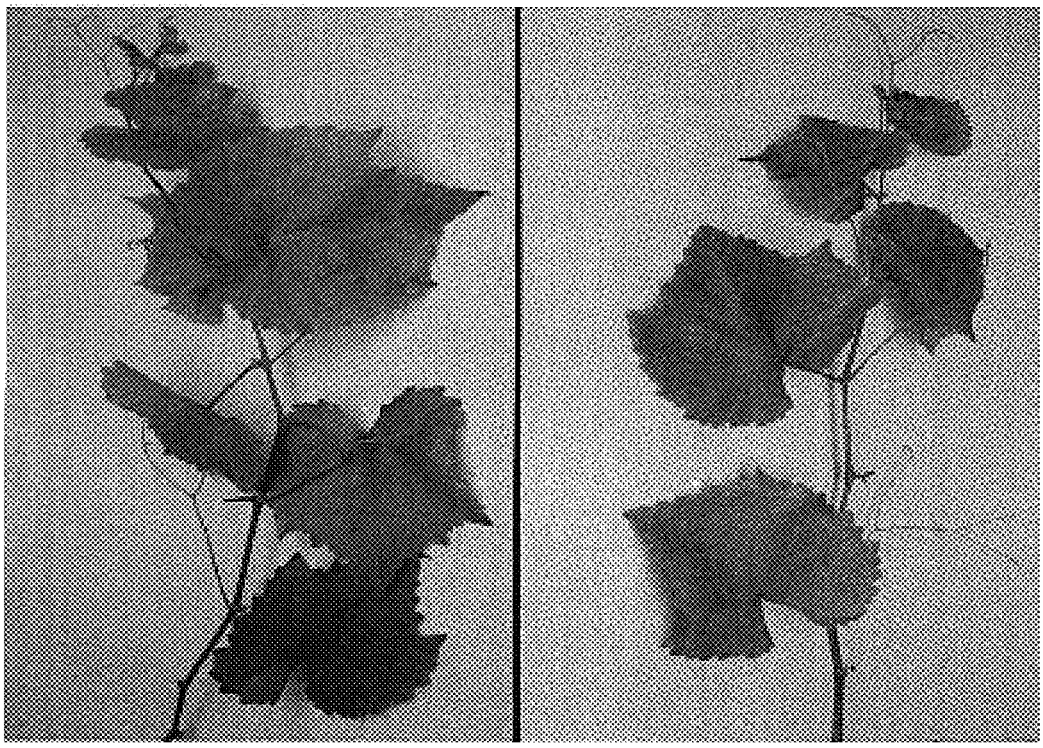
FIG. 1 Shows canes, leaves, and tendrils of 'Improved Chancellor' (left) in comparison to the parent (right)
Figure 2:
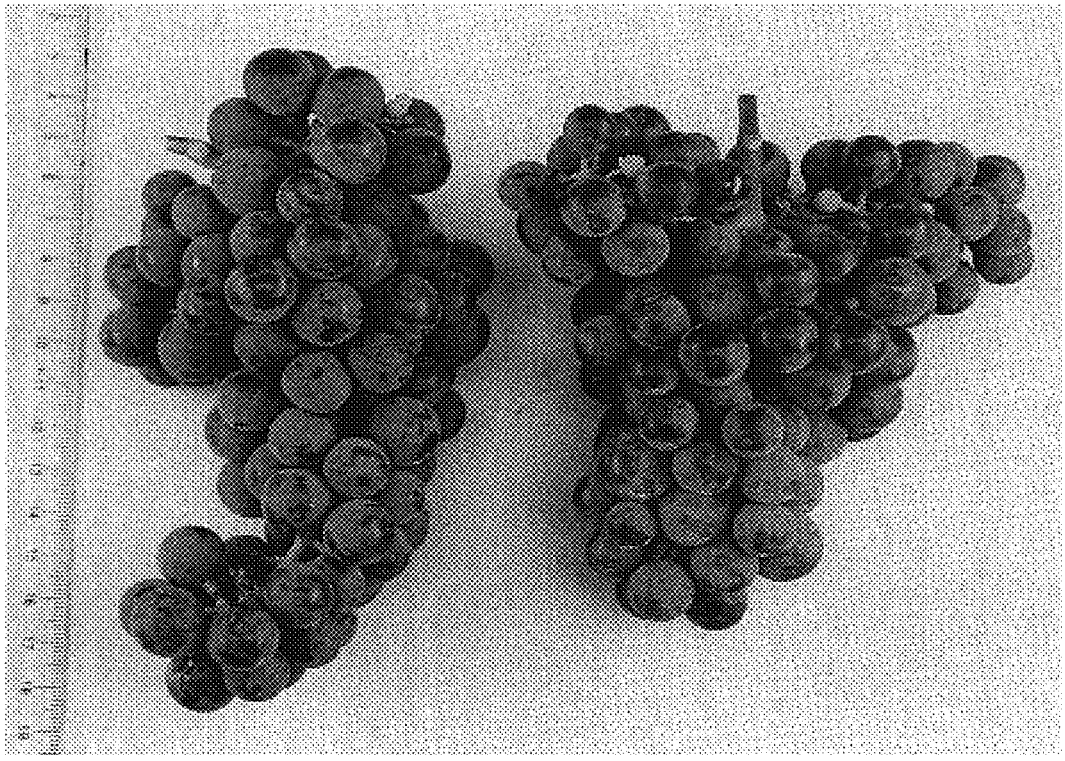
FIG. 2 Shows fruit clusters of parental 'Chancellor' at harvest.

The following description of grapevine contains references to color names taken from the Ridgeway Color Standards and Color Nomenclature (1912, Hoen and Co., Baltimore, Md.). Descriptors used herein conform to those set forth by the International Board for Plant Genetic Resources Institute Grape Descriptors (*Vitis* spp.) of 1983 and/or 1997 which were developed in collaboration with the Office International de la Vigne et du Vin (OIV) and the International Union for the Protection of New Varieties of Plants (UPOV) and published in Descriptors for Grapevine (*Vitis* spp.) (Anonymous, International Plant Genetic Resources Institute, 1997, ISBN 92-9043-352-3).

Descriptions of the new invention apply to vines of 'Improved Chancellor' grown in an isolation greenhouse in the year 2005. These vines were in their first year of growth having been transplanted from in vitro to the greenhouse in December 2004. The parent clones (control) were growing on their own roots in Urbana, Ill. The descriptions of the parent plants apply generally to the new variety grown under similar circumstances elsewhere:

VINE

General:

*Vigor.*—Too young to give valid data.
*Productivity.*—Unavailable.
*Hardiness.*—Unavailable.
*Rootstock.*—None.

LEAVES

Mature leaves: Average blade length 8.6 cm. Average blade width 12.5 cm.

*Size of blade.*—Large.
*Shape.*—Pentagonal. Anthocyanin coloration of main veins on the upper side of the blade. Present at base of veins on mature leaves, Dahlia Purple, 67.V-R.m Plate XII.
*Anthocyanin coloration of main veins on lower leaf surface.*—Clear Yellow Green, 31.Y-G. Plate VI.
*Mature leaf profile.*—Undulating.
*Blistering surface of blade upper surface.*—Absent.
*Leaf blade tip.*—Curved downward.
*Margins.*—Serrate.
*Apex.*—Acuminate.
*Base.*—Sagittate.
*Thickness.*—0.06552 in.
*Undulation of blade between main and lateral veins.*—Medium.
*Shape of teeth.*—Conical, both sides convex.
*Length of teeth.*—3.8 mm.
*Ratio length/width of teeth.*—About 1:1.6.
*General shape of petiole sinus.*—Y-shaped.
*Tooth at petiole sinus.*—Absent.
*Petiole sinus limited by veins.*—Absent.
*Shape of upper lateral sinus.*—Open Y-shaped.
*Prostrate hairs between veins on lower surface of blade.*—Absent.
*Erect hairs between veins on lower surface of blade.*—Absent.

*Prostrate hairs on main veins on lower surface of blade.*—Present.
*Density of erect hairs on main veins on lower surface of blade.*—Sparse.
*Prostrate hairs on main veins on upper surface of blade.*—Absent.

Upper surface:
*Summer color.*—Civette green, 31' Y-G. Plate XVIII.
*Autumn color.*—Variety's Green, 31'. Y-G Plate XVIII.
*Surface texture.*—Smooth.
*Surface appearance.*—Medium glossy.
*Goffering of blade.*—Medium on mature leaves.

Lower surface:
*Summer color.*—Mineral green, 31'. Y-G. i Plate XVIII.
*Autumn color.*—Grass Green, 33. G-YG Plate VI.
*Anthocyanin coloration of main veins on lower leaf surface.*—Clear Yellow Green, 31. YG Plate VI.
*Glossiness.*—Low.
*Pubescence.*—Mildly present.
*Surface texture.*—Medium leathery.
*Surface appearance.*—Dull.

Petiole:
*Length of petiole.*—5.8 cm — mean of 10 petioles.
*Diameter.*—2.2 mm — mean of 10 petioles.
*Fall color.*—Varies along petiole from Deer Rose Pink, 71. V-RR. Plate XII) to Amaranth Purple, 69. Rv-R Plate XII.
*Length of petiole compared to middle vein.*—In fall petioles are about 50% to 100% longer than the vein.
*Density of prostrate hairs on petiole.*—Sparse on young leaves; absent on mature leaves.
*Density of erect hairs on petiole.*—Dense on young leaves.
*Shape of base of petiole sinus.*—Mostly open, with inside outline ovate.

TENDRILS
*Number.*—Tendrils at all nodes above node #2; abort on older growth.
*Length.*—14.8 cm.
*Diameter.*—1.4 mm.
*Texture.*—Smooth.
*Color.*—Mineral green, 31'. Y-G. i Plate XVIII, with occasional Brown vinaceous, 5'".OO-R Plate XXXIX to Pale Veronese Green, 31'. Y-G, Plate XVIII.

WOODY SHOOT

Trunk:
*Trunk circumference.*—0.4 cm. at 1 meter height. Mean of 10 plants.
*Shape.*—Circular.
*Surface texture.*—Smooth — canes still young.
*Outer bark color.*—Vinaceous Tawny, 11" orange Plate XXVIII.

Canes:
*Shape of canes in cross section.*—Broadly elliptical.
*Internode length.*—6.7 cm. Mean of 10 canes counting nodes #3–6.
*Width at node.*—About 0.75 cm. Mean of 10 canes measuring nodes #3–6.
*Surface.*—Smooth.
*Main color.*—Bright Clalcedony Yellow, 25' YG-Y-i Plate XVII.
*Fall color.*—Carob brown, 9'. OR-O Plate XIV.
*Lenticels.*—Inconspicuous.
*Erect hairs on nodes.*—Absent.
*Erect hairs on internodes.*—Absent.
*Growth of axillary shoots.*—Moderately prolific.
*Shape of nodes in cross section.*—Circular to broadly elliptical.
*Number.*—Lateral shoots generally develop at all nodes above node #5.
*Length.*—Grow to about 0.5 to 1 m.
*Diameter.*—2.9 mm — mean of 10 laterals.
*Internode length.*—6.3 cm — mean of 10 canes.
*Color.*—Wintergreen, 33'.GY-G, Plate XVIII to Dark Maroon Purple, 71'.V-RR, Plate XXVI.

Buds:
*Shape.*—Conical.
*Length.*—2.8 mm. — mean of 9 buds node.
*Width.*—3.2 mm. mean of 9 buds node.
*Color.*—Vinaceous Tawny, 11" orange Plate XXVIII.

FLOWERS — Data from mature field parent 'Chancellor' plants

General:
*Flower sex.*—Perfect.
*Length of first inflorescence.*—5.2 cm. — Mean of 7 inflorescences.
*Position of first flowering nodes.*—2–4.
*Number of inflorescences per shoot.*—# 1 TO 2.
*Pedicel length.*—2.3 mm. — Mean of 10 pedicels.
*Calyptra color.*—Light Turtle green, 31". Y-G Plate XXXII.
*Ovary length.*—1.5 mm. — Mean of 10 ovaries.
*Ovary width.*—1.2 mm. — Mean of 10 ovaries.
*Ovary color.*—Light fluorite green, 33".GY-G., Plate XXXII.
*Filament length.*—1.9 mm. Composite mean of single filaments each from 5 flowers.
*Filament color.*—Pale Turtle Green, 31". Y-G Plate XXXII.
*Anther length.*—0.55 mm. Composite mean of 4 anthers each from 4 flowers.
*Anther color.*—Cream color 19'.YO-Y. f Plate XVI.

FRUIT

Herbicide resistance: Significantly greater resistance to phenoxy herbicides (especially 2,4 diphenoxyacetic acid) than parent 'Chancellor' grapevine. The resistance in the 'Improved Chancellor' is due to its genetic modification to contain and express the tfdA coding sequence. Transgenic plants survived treatment with 0.5, 5, and 10 kg $ha^{-1}$ of the 2-ethylhexyl ester of 2, 4-D. These rates killed non-transgenic plants.

References:

Anonymous. International Plant Genetic Resources Institute, 1997, ISBN 92-9043-352-3

Murashige, T. and F. Skoog. 1962. A revised medium for rapid growth and bio-assays with tobacco tissue cultures. Physiologia Plantarum, 15: 473–497.

Nistch, J. P. and C. Nistch. 1969. Haploid plants from pollen grains. Science, 163: 85–87.

Ridgeway, R. 1912. Color standards and color nomenclature. A. Hoen and Company, Baltimore, Md.

Skirvin, R. M., M. A. Norton, A. G. Otterbacher, R. Mulwa, B. Shoemaker, B. Aly, and E. Wahle. 2005. Grape varieties for the different regions of Illinois — 2005. Proceedings 2005 Illinois Small Fruit & Strawberry Schools. NRES 7:29–40.

What is claimed is:

1. A new and distinct variety of grape plant named 'Improved Chancellor' as herein illustrated and described.

* * * * *

UNITED STATES PATENT AND TRADEMARK OFFICE

CERTIFICATE OF CORRECTION

PATENT NO. : PP20,428 P3
APPLICATION NO. : 11/206645
DATED : October 20, 2009
INVENTOR(S) : Robert M. Skirvin et al.

It is certified that error appears in the above-identified patent and that said Letters Patent is hereby corrected as shown below:

In the drawings insert fig 3.

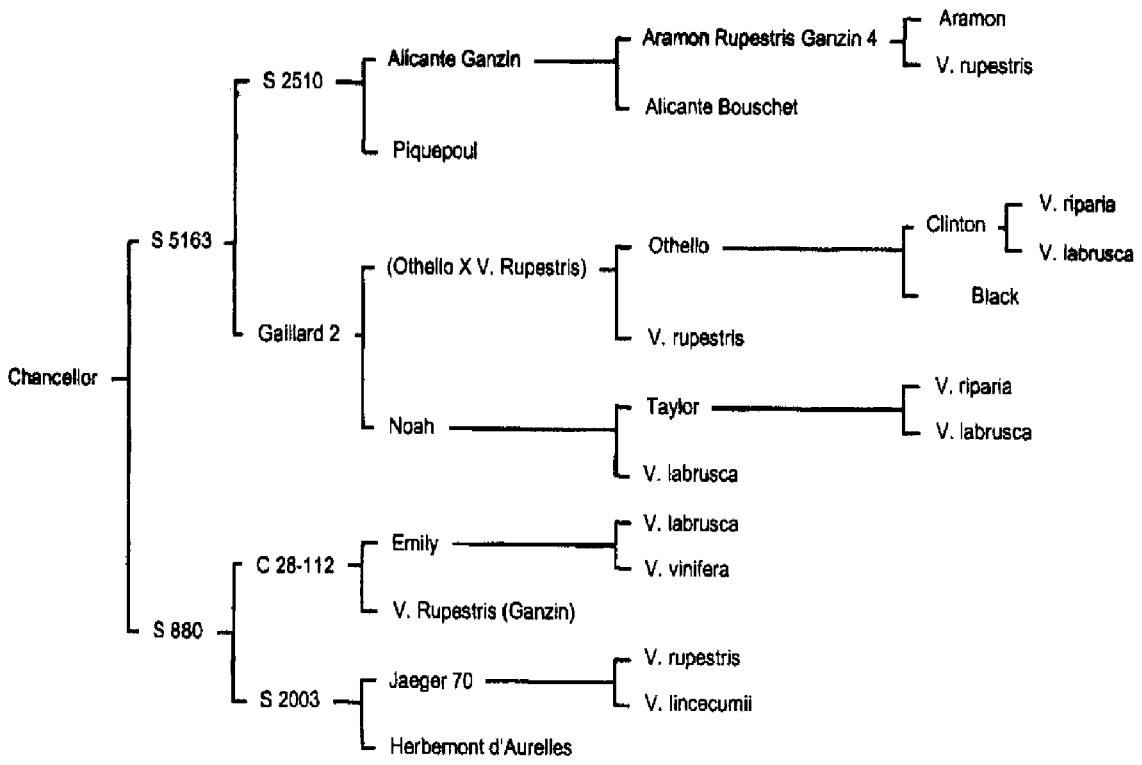

Fig. 3

Signed and Sealed this
Eighth Day of March, 2011

David J. Kappos

David J. Kappos
*Director of the United States Patent and Trademark Office*